(12) United States Patent
Nagasawa et al.

(10) Patent No.: US 9,084,419 B2
(45) Date of Patent: *Jul. 21, 2015

(54) METHOD FOR REDUCING TEMPERATURE STRESS OF PLANTS

(75) Inventors: Asako Nagasawa, Kobe (JP); Fujio Mukumoto, Kobe (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/514,791

(22) PCT Filed: Dec. 9, 2010

(86) PCT No.: PCT/JP2010/072599
§ 371 (c)(1),
(2), (4) Date: Aug. 2, 2012

(87) PCT Pub. No.: WO2011/071187
PCT Pub. Date: Jun. 16, 2011

(65) Prior Publication Data
US 2012/0295791 A1    Nov. 22, 2012

(30) Foreign Application Priority Data
Dec. 11, 2009  (JP) ................. 2009-281348

(51) Int. Cl.
*A01N 37/30* (2006.01)

(52) U.S. Cl.
CPC ................... *A01N 37/30* (2013.01)

(58) Field of Classification Search
CPC ............... A01N 37/30; A01N 25/00
See application file for complete search history.

(56) References Cited

U.S. PATENT DOCUMENTS

| 5,298,482 A | 3/1994 | Tanaka et al. |
| 6,432,883 B1 | 8/2002 | Kinnersley |
| 2012/0122677 A1* | 5/2012 | Kurahashi ................ 504/100 |

FOREIGN PATENT DOCUMENTS

| CN | 101416626 A | 4/2009 |
| JP | 4-338305 A | 11/1992 |
| JP | 11-199419 A | 7/1999 |
| JP | 11-255607 A | 9/1999 |
| JP | 2001-139405 A | 5/2001 |
| JP | 2003-525202 A | 8/2003 |
| JP | 2003-535053 A | 11/2003 |
| JP | 2005-192534 A | 7/2005 |
| JP | 408794 B2 | 5/2008 |
| JP | 2009-55834 A | 3/2009 |
| WO | WO 99/45774 A1 | 9/1999 |
| WO | WO 00/19821 A1 | 4/2000 |
| WO | WO 01/80637 A1 | 11/2001 |
| WO | WO 2009/055044 A1 | 4/2009 |
| WO | WO 2011/119681 A | 9/2011 |
| WO | WO 2012/046821 A1 | 4/2012 |

OTHER PUBLICATIONS

Japanese Patent Office machine translation of JP-11-255607-A (1999).*
International Search Report issued in PCT/JP2010/072599 dated Jan. 25, 2011.
Written Openion issued in PCT/JP2010/072599, dated Jan. 25, 2011.
The Office Action (including English translation), dated Jun. 21, 2013, issued in corresponding Chinese Patent Application No. 201080056097.8.
The Search Report, dated Jul. 31, 2013, issued in corresponding European Patent Application No. 10836104.9.
Itagaki et al., "Biological activities and structure-activity relationship of substitution compounds of N-[2[(3-indolyl)ethyl]succinamic acid and N-[2-(1-naphthyl)ethyl]succinamic acid, derived from a new category of root-promoting substances, N-(phenethyl)succinamic acid analogs," Plant and Soil, vol. 255, pp. 67-75, 2003.
Machine-Generated Translation for JP-11-199419-A, published Jul. 27, 1999.
Machine-Generated Translation for JP-11-255607-A, published Sep. 21, 1999.
Machine-Generated Translation for JP-2001-139405-A, published on May 22, 2001.
Machine-Generated Translation for JP-2005-192534-A, published on Jul. 21, 2005.
The Second Office Action (including English translation), dated Jan. 16, 2014, issued in the corresponding Chinese Patent Application No. 201080056097.8.
The Third Office Action (including English translation), dated Apr. 10, 2014, issued in the corresponding Chinese Patent Application No. 201080056097.8.
The Rejection Decision (including an English translation), dated Aug. 5, 2014, issued in the corresponding Chinese Patent Application 201080056097.8.
The Office Action (including an English translation), dated Jun. 23, 2014, issued in the corresponding Mexican Patent Application No. MX/a/2012/006444.
The Details of the Reexamination Notification (including an English translation), dated Mar. 27, 2015, issued in the corresponding Chinese Patent Application No. 201080056097.8.

(Continued)

*Primary Examiner* — Bethany Barham
*Assistant Examiner* — Peter Anthopolos
(74) *Attorney, Agent, or Firm* — Birch, Stewart, Kolasch & Birch, LLP

(57) ABSTRACT

The present invention provides: a method for reducing temperature stress of plants which comprises applying an effective amount of one or more compounds selected from the group consisting of a compound represented by the formula (I) and an agriculturally acceptable salt thereof to a plant that has been exposed to or to be exposed to a temperature stress factor; and so on.

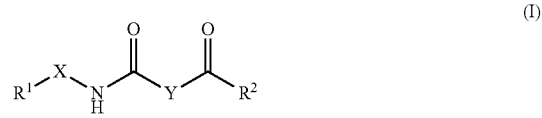

(I)

5 Claims, No Drawings

(56) References Cited

OTHER PUBLICATIONS

The Office Action (including an English translation), dated Oct. 28, 2014, issued in the corresponding Japanese Patent Application No. 2010-273299.

The Office Action (including an English translation) issued in the corresponding Egyptian Patent Application No. 2012050970 on Jan. 26, 2015.

* cited by examiner

METHOD FOR REDUCING TEMPERATURE STRESS OF PLANTS

TECHNICAL FIELD

The present invention relates to a method for reducing temperature stress of plants.

BACKGROUND ART

When plants encounter an environment where the temperature exceeds the upper limit or the lower limit of an optimal temperature for growth or germination, what is called temperature stress factor, physiological functions of cells decline slowly or rapidly and thus various disorders may arise. While it has been known that phytohormones and some chemical substances such as plant growth regulators have an effect of reducing temperature stress of plants, these substances cannot be said to be sufficient in terms of their effects. It has also been known that 4-oxo-4-[(2-phenylethyl)amino]-butyric acid and derivatives thereof have activity to promote growth of roots (see, for example, Japanese Patent Publication No. 4,087,942, Japanese Unexamined Patent Publication No. 2001-139405, and Plant and Soil, 255: 67-75, (2003)). However, an effect of reducing temperature stress of plants has never been known.

DISCLOSURE OF INVENTION

An object of the present invention is to provide a method for reducing temperature stress of plants, and so on.

The present invention is based on the finding that plants that has been applied with a specified compound has a reduction in temperature stress even when the plants are exposed to a temperature stress factor.

That is, the present invention includes the following constitutions.

[1] A method for reducing temperature stress of plants which comprises applying an effective amount of one or more compounds selected from the group consisting of a compound represented by the formula (I) and an agriculturally acceptable salt thereof (hereinafter, sometimes referred to as the present compound) to a plant that has been exposed to or to be exposed to a temperature stress factor (hereinafter, sometimes referred to as the method of the present invention):

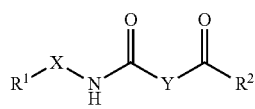

(I)

wherein $R^1$ represents a phenyl group, a naphthyl group or an aromatic heterocyclic group, and these groups are optionally substituted with 1 to 5 members selected from among a halogen atom, a hydroxyl group, a cyano group, a nitro group, a C1-C6 alkyl group optionally substituted with one or more halogen atoms, a C1-C6 alkoxy group optionally substituted with one or more halogen atoms, a C1-C6 alkylthio group optionally substituted with one or more halogen atoms, a C2-C6 alkenyl group optionally substituted with one or more halogen atoms, a C2-C6 alkynyl group optionally substituted with one or more halogen atoms, an amino group, a C1-C6 alkylamino group and a di(C1-C6 alkyl)amino group;

$R^2$ represents a hydroxyl group, an amino group, or a C1-C6 alkoxy group;

X represents a linear or branched C1-C6 alkylene group; and

Y represents a linear or branched C1-C6 alkylene group, or a linear or branched C1-C6 alkenylene group.

[2] The method according to [1], wherein in the formula (I),
$R^1$ is a phenyl group, a 1-naphthyl group or a 3-indolyl group, wherein one or more hydrogen atoms in these groups are optionally replaced by 1 to 5 members selected from among a halogen atom, a hydroxyl group, a nitro group, a C1-C6 alkyl group and a C1-C6 alkoxy group;
$R^2$ is a hydroxyl group, an amino group or a C1-C6 alkoxy group;
X is a linear or branched C1-C6 alkylene group; and
Y is a linear or branched C1-C6 alkylene group, or a linear or branched C1-C6 alkenylene group.

[3] The method according to [1], wherein in the formula (I),
$R^1$ is a phenyl group, a 4-iodophenyl group, a 1-naphthyl group or a 3-indolyl group;
$R^2$ is a hydroxyl group or a methoxy group;
X is an ethylene group or a tetramethylene group; and
Y is an ethylene group or a trimethylene group.

[4] The method according to [1], wherein the compound of the formula (I) is a compound selected from among the following compounds:
(1) 4-oxo-4-(2-phenylethyl)aminobutyric acid (hereinafter, sometimes referred to as the compound A),
(2) methyl 4-oxo-4-(4-phenylbutyl)aminobutyrate (hereinafter, sometimes referred to as the compound B),
(3) methyl 4-oxo-4-(2-phenylethyl)aminobutyrate (hereinafter, sometimes referred to as the compound C),
(4) 4-oxo-4-(4-phenylbutyl)aminobutyric acid (hereinafter, sometimes referred to as the compound D),
(5) 5-oxo-5-[2-(3-indolyl)ethyl]aminovaleric acid (hereinafter, sometimes referred to as the compound E),
(6) 5-oxo-5-[(1-naphthyl)methyl]aminovaleric acid (hereinafter, sometimes referred to as the compound F), and
(7) methyl 4-oxo-4-[2-(4-iodophenyl)ethyl]aminobutyrate (hereinafter, sometimes referred to as the compound G).

[5] The method according to any one of [1] to [4], wherein the application is a soil irrigation treatment, a spraying treatment, a hydroponic treatment or a seed treatment.

[6] The method according to any one of [1] to [5], wherein the application is a seed treatment.

[7] The method according to [6], wherein an application amount of the compound of the formula (I) in the seed treatment is from 30 g to 500 g per 100 kg of seeds.

[8] The method according to any one of [1] to [7], wherein the plant is rice, corn, soybean, wheat or tomato.

[9] The method according to any one of [1] to [8], wherein the plant is a transgenic plant.

[10] The method according to any one of [1] to [9], wherein the temperature stress is high temperature stress.

[11] The method according to any one of [1] to [9], wherein the temperature stress is low temperature stress.

[12] The method according to any one of [1] to [11], wherein the temperature stress is indicated by a change in one or more of the following plant phenotypes:
(1) germination percentage,
(2) seedling establishment rate,
(3) number of healthy leaves,
(4) plant length,
(5) plant weight,
(6) leaf area,
(7) leaf color,
(8) number or weight of seeds or fruits,
(9) quality of harvests,
(10) flower setting rate or fruit setting rate, and
(11) chlorophyll fluorescence yield;

[13] Use of one or more compounds selected from the group consisting of a compound represented by the formula (I) of [1] and an agriculturally acceptable salt thereof for reducing temperature stress of plants.

[14] The use according to [13], wherein the temperature stress is indicated by a change in one or more of the following plant phenotypes:
(1) germination percentage,
(2) seedling establishment rate,
(3) number of healthy leaves,
(4) plant length,
(5) plant weight,
(6) leaf area,
(7) leaf color,
(8) number or weight of seeds or fruits,
(9) quality of harvests,
(10) flower setting rate or fruit setting rate, and
(11) chlorophyll fluorescence yield.

Use of the method of the present invention enables reduction of temperature stress of plants.

MODE FOR CARRYING OUT THE INVENTION

In the present invention, generically referred to as a "temperature stress" factor is an environmental factor which causes decline in a physiological function of plant cells as a result of exposure of a plant to a temperature environment that deviates from an optimal temperature where the temperature exceeds the upper limit or the lower limit of an optimal temperature for growth or germination of the plant. The temperature stress factor is referred to as a high temperature stress factor in the case where the temperature exceeds the upper limit of the optimal temperature, while the temperature stress factor is referred to as a low temperature stress factor in the case where the temperature exceeds the lower limit of the optimal temperature. The optimal temperature for growth or optimal temperature for germination of plants vary depending on plants and, generally, the optimal temperature for germination is often higher than the optimal temperature for growth.

The temperature stress of plants can be monitored by a comparison in a change in the following plant phenotypes between plants which are not exposed to a temperature stress factor and plants exposed to the temperature stress factor. That is, the plant phenotypes serve as indicators of the temperature stress of plants.

<Plant Phenotypes>
(1) germination percentage
(2) seedling establishment rate
(3) number of healthy leaves
(4) plant length
(5) plant weight
(6) leaf area
(7) leaf color
(8) number or weight of seeds or fruits
(9) quality of harvests
(10) flower setting rateor fruiting rate, and
(11) chlorophyll fluorescence yield In the present specification, the temperature stress may be quantified by determining the "intensity of stress" represented by the following equation.

"Intensity of stress"=100×"any one of plant phenotypes in plants which are not exposed to a temperature stress factor"/"the plant phenotype in plants exposed to a temperature stress factor"    Equation:

The method of the present invention is applied to plants that have been exposed to or to be exposed to a temperature stress factor whose "intensity of stress" represented by the above equation is from 105 to 200, preferably from 110 to 180, and more preferably from 120 to 160.

When plants are exposed to the temperature stress factor, one or more of the above phenotypes varies. That is, due to the temperature stress:
(1) decrease in germination percentage,
(2) decrease in seedling establishment rate,
(3) decrease in number of healthy leaves,
(4) decrease in plant length,
(5) decrease in plant weight,
(6) decrease in leaf area increasing rate,
(7) leaf color fading,
(8) decrease in number or weight of seeds or fruits,
(9) decline in quality of harvests,
(10) decrease in flower setting rate or fruit setting rate, and
(11) decrease in chlorophyll fluorescence yield;
are observed and the magnitude of the temperature stress of plants can be measured using these as indicators. The present invention is directed to a method for reducing an influence of a temperature stress factor on plants that have been exposed to or to be exposed to the temperature stress factor by applying the compound represented by the formula (I) to the plants. The effect of reducing the temperature stress can be evaluated by a comparison of the indicator after the plants are exposed to the temperature stress factor between plants treated with the compound represented by the formula (I) and plants which are not treated.

Stages in which target plants in the present invention can be exposed to the temperature stress factor include all growth stages of plants, including a germination period, a vegetative growing period, a reproductive growing period and a harvesting period. The application period of the present compound used in the present invention may be any growth stage of plants, and examples thereof include the germination period such as before seeding, at the time of seeding, and after seeding and before or after emergence; the vegetative growing period such as at the time of seedling raising, at the time of seedling transplantation, at the time of cuttage or sticking, or at the time of growing after settled planting; the reproductive growing period such as before blooming, during blooming, after blooming, immediately before earing or during the earing period; and the harvesting period such as before harvesting plan, before ripening plan, or a coloration initiation period of fruits. Plants to which the present compound is to be applied may be plants that have been exposed to or to be exposed to the temperature stress factor. That is, the present compound can also be preventively applied to plants before being exposed to the temperature stress factor in addition to plants exposed to the temperature stress factor.

The present compound used in the method of the present invention is one or more compounds selected from the group consisting of a compound represented by the following formula (I):

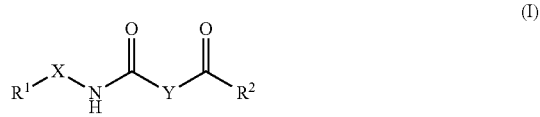

wherein
$R^1$ represents a phenyl group, a naphthyl group or an aromatic heterocyclic group, and these groups are optionally substituted with 1 to 5 members selected from among a halogen atom, a hydroxyl group, a cyano group, a nitro group, a C1-C6 alkyl group optionally substituted with one or more halogen atoms, a C1-C6 alkoxy group optionally substituted with one or more halogen atoms, a C1-C6 alkylthio group optionally substituted with one or more halogen atoms, a C2-C6 alkenyl group optionally substituted with one or more halogen atoms, a C2-C6 alkynyl group optionally substituted with one or more halogen atoms, an amino group, a C1-C6 alkylamino group and a di(C1-C6 alkyl)amino group;

$R^2$ represents a hydroxyl group, an amino group, or a C1-C6 alkoxy group;

X represents a linear or branched C1-C6 alkylene group; and

Y represents a linear or branched C1-C6 alkylene group, or a linear or branched C1-C6 alkenylene group; and an agriculturally acceptable salt thereof.

The compound represented by the formula (I) is a compound described in Japanese Patent Publication No. 4087942 or Japanese Unexamined Patent Publication No. 2001-139405 and can be synthesized, for example, by the method described in the publications.

The present compound is preferably one or more compounds selected from the group consisting of the compound of the formula (I), wherein in the formula (I), $R^1$ is a phenyl group, a 1-naphthyl group or a 3-indolyl group, wherein one or more hydrogen atoms in these groups are optionally replaced by 1 to 5 members selected from among a halogen atom, a hydroxyl group, a nitro group, a C1-C6 alkyl group and a C1-C6 alkoxy group;

$R^2$ is a hydroxyl group, an amino group or a C1-C6 alkoxy group;

X is a linear or branched C1-C6 alkylene group; and

Y is a linear or branched C1-C6 alkylene group, or a linear or branched C1-C6 alkenylene group; and an agriculturally acceptable salt thereof.

The present compound is more preferably one or more compounds selected from the group consisting of the compound of the formula (I), wherein in the formula (I), $R^1$ is a phenyl group, a 4-iodophenyl group, a 1-naphthyl group or a 3-indolyl group;

$R^2$ is a hydroxyl group or a methoxy group;

X is an ethylene group or a tetramethylene group; and

Y is an ethylene group or a trimethylene group; and an agriculturally acceptable salt thereof.

Specific examples of the present compound include:
(1) 4-oxo-4-(2-phenylethyl)aminobutyric acid,
(2) methyl 4-oxo-4-(4-phenylbutyl)aminobutyrate,
(3) methyl 4-oxo-4-(2-phenylethyl)aminobutyrate,
(4) 4-oxo-4-(4-phenylbutyl)aminobutyric acid,
(5) 5-oxo-5-[2-(3-indolyl)ethyl]aminovaleric acid,
(6) 5-oxo-5-[(1-naphthyl)methyl]aminovaleric acid, and
(7) methyl 4-oxo-4-[2-(4-iodophenyflethyl]aminobutyrate,
  and the compound is preferable from the viewpoint that it is capable of effectively reducing temperature stress of plants.

The compound represented by the formula (I) may be a salt with a base. Examples of a basic salt of the compound represented by the formula (I) include the followings:

metal salts such as alkali metal salts and alkaline earth metal salts, including salts of sodium, potassium or magnesium;

salts with ammonia; and salts with organic amines such as morpholine, piperidine, pyrrolidine, mono-lower alkylamine, di-lower alkylamine, tri-lower alkylamine, monohydroxy lower alkylamine, dihydroxy lower alkylamine and trihydroxy lower alkylamine.

The present compound used in the method of the present invention can be used alone, or used after being formulated using various inert ingredients as described hereinafter.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The method of the present invention is usually carried out by applying an effective amount of the present compound to plants or growing sites of plants. Examples of the plant to which the present compound is to be applied include foliages, buds, flowers, fruits, ears or spikes, seeds, bulbs, stem tubers, roots and seedlings. As used herein, bulbs mean discoid stem, corm, rhizoma, root tuber and rhizophore. In the present specification, the seedlings include cutting and sugar cane stem cutting. Examples of growing sites of plants include soil before or after sowing plants. When the present compound is applied to plants or growing sites of plants, the compound is applied to the target plants once or more than once.

Specific examples of the application method in the method of the present invention include treatment of foliages, floral organs or ears or spikes of plants, such as foliage spraying; treatment of cultivation lands of plants such as soil treatment; treatment of seeds such as seed sterilization, seed immersion or seed coating; treatment of seedlings; and treatment of bulbs such as seed tuber.

Specific examples of the treatment of foliages, floral organs or ears or spikes of plants in the method of the present invention include the treatment method of applying the compound to the surface of plants, such as foliage spraying or trunk spraying. Examples of the treatment also include a method of spraying the compound to the floral organ or entire plants in the blooming season including before blooming, during blooming and after blooming. Examples of the treatment in cereals and the like include a method of spraying the compound to the ear or spikes or entire plants in the earing season.

Examples of the soil treatment method in the method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the above soil treatment, more than one kinds of the present compounds may be simultaneously applied to the plant, or a solid fertilizer such as a paste fertilizer containing the present compound may be applied to the soil. Also, the present compound may be mixed in an irrigation liquid, and, examples thereof include injecting to irrigation facilities such as irrigation tube, irrigation pipe and sprinkler, mixing into the flooding liquid between furrows and mixing into a hydroponic medium. Alternatively, an irrigation liquid may be mixed with the present compound in advance and, for example, used for treatment by an appropriate irrigating method including the irrigating method mentioned above and the other methods such as sprinkling and flooding. Alternatively, the present compound can be applied by winding a crop with a sheet or a string of a resin formulation, putting a string of the resin formulation around a crop so that the crop is surrounded by the string, and/or laying a sheet of the resin formulation on the soil surface near the root of a crop.

Examples of the method of treating seeds in the method of the present invention include a method for treating seeds or bulbs of a plant to be protected from temperature stress with the present compound and specific examples thereof include a spraying treatment in which a suspension of the present compound is atomized and sprayed on the seed surface or the bulb surface, a smearing treatment in which a wettable powder, an emulsion or a flowable agent of the present compound is applied to seeds or bulbs with a small amount of water added or applied as it is without dilution, an immersing treatment in which seeds are immersed in a solution of the present compound for a certain period of time, film coating treatment, and pellet coating treatment.

Examples of the treatment of seedlings in the method of the present invention include spraying treatment of spraying to the entire seedlings a dilution having a proper concentration of active ingredients prepared by diluting the present compound with water, immersing treatment of immersing seedlings in the dilution, and coating treatment of adhering the present compound formulated into a dust formulation to the entire seedlings. Examples of the method of treating the soil before or after sowing seedlings include a method of spraying a dilution having a proper concentration of active ingredients prepared by diluting the present compound with water to seedlings or the soil around seedlings after sowing seedlings, and a method of spraying the present compound formulated into a solid formulation such as a granule to soil around seedlings after sowing seedlings.

The present compound may be mixed with a hydroponic medium in hydroponics, and may also be used as one of culture medium components in tissue culture. When the present compound is used for hydroponics, it can be dissolved or suspended in a conventionally used culture medium for hydroponics, such as ENSHI, at a concentration within a range from 0.001 to 10,000 ppm. When the present compound is used at the time of tissue culture or cell culture, it can be dissolved or suspended in a conventionally used culture medium for plant tissue culture, such as an MS culture medium, at a concentration within a range from 0.001 to 10,000 ppm. In this case, in accordance with a usual method, saccharides as a carbon source, various phytohormones and the like can be appropriately added.

When the present compound is used for treatment of plants or growing sites of plants, the treatment amount can vary depending on the kind of plants to be treated, formulation form, treating period and meteorological conditions, but is usually within a rang from 0.1 to 1,000 g, and preferably from 1 to 500 g, in terms of an active ingredient amount, per 1,000 $m^2$. When the present compound is incorporated into the entire soil, the treatment amount is usually within a range from 0.1 to 1,000 g, and preferably from 1 to 500 g, in terms of an active ingredient amount, per 1,000 $m^2$.

An emulsion, a wettable powder, a flowable agent and a microcapsule are usually used for the treatment by spraying after dilution with water. In this case, the concentration of the active ingredient is usually within a range from 0.01 to 10,000 ppm, and preferably from 1 to 5,000 ppm. A dust formulation and a granule are usually used for the treatment as they are without dilution.

In the treatment of seeds, the weight of the present compound per seed is usually within a range from 0.0001 to 5 mg, and preferably from 0.005 to 1 mg, and the weight of the present compound per 100 kg of seeds is usually within a range from 5 to 1,000 g, and preferably from 30 to 500 g, and more preferably from 50 to 200 g. When seeds are subjected to an immersing treatment, the present compound can be used after being dissolved or suspended at a concentration of the active ingredient within a range from 0.01 to 10,000 ppm.

In the treatment of seedlings, the weight of the present compound per seedling is usually within a range from 0.01 to 20 mg, and preferably from 0.1 to 10 mg. In the treatment of the soil before or after sowing seedlings, the weight of the present compound per 1,000 $m^2$ is usually within a range from 0.1 to 100 g, and preferably from 1 to 50 g.

Examples of plants whose temperature stress can be reduced by the present invention include the followings.

crops: corn, rice, wheat, barley, rye, oat, sorghum, cotton, soybean, peanut, buckwheat, beet, canola, rapeseed, sunflower, sugar cane, tobacco, and pea, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, Dioscorea japonica, colocasia, etc.;

flowers;

foliage plants;

turf grasses;

fruits: pomaceous fruits (apple, pear, Japanese pear, Chinese quince, quince, etc.), stone fleshy fruits (peach, plum, nectarine, Prunus mume, cherry fruit, apricot, prune, etc.), citrus fruits (Citrus unshiu, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, Eucalyptus, Ginkgo biloba, lilac, maple, Quercus, poplar, Judas tree, Liquidambar formosana, plane tree, zelkova, Japanese arborvitae, fir wood, hemlock, juniper, *Pinus, Picea*, and *Taxus cuspidate*), etc.

Examples of plants whose temperature stress can be reduced by the present invention preferably include rice, corn, soybean, wheat and tomato.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soybean on which resistance to sulfonylurea ALS inhibitory herbicides such as thifensulfuron-methyl has been conferred by a classical breeding method, which is already commercially available under a product name of STS soybean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soybean, cotton, rape, sugar beet resistant to glyphosate, which is already commercially available under a product name of RoundupReady (registered trademark), AgrisureGT, etc. Similarly, there are corn, soybean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to Coleoptera, Hemiptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Boilgard I (registered trademark) (a cotton variety for expressing Cry1Ac toxin), Boilgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Btll corn borer (CB) trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

In the case where plants are exposed to a temperature higher than the optimal temperature for growth or the optimal temperature for germination, the physiological metabolism function in vivo declines and growth or germination is inhibited to cause a decrease in vitality of the plants, resulting in a state of being exposed to a high temperature stress factor. Specifically, in the case where plants are in a growing period, the conditions which lead to the high temperature stress may be conditions in which an average cultivation temperature in an environment where plants are cultivated is 25° C. or higher, more severely 30° C. or higher, and still more severely 35° C. or higher. The present invention is capable of providing a method for reducing temperature stress of plants under these high temperature stress conditions. Reduction of the temperature stress of plants can be evaluated by measuring an improvement in the indicators which show the temperature stress.

In the case where plants are exposed to the temperature lower than the optimal temperature for growth or the optimal temperature for germination, physiological metabolism function in vivo declines and growth or germination is inhibited to cause a decrease in vitality of the plants, resulting in a state of being exposed to a low temperature stress factor. Specifically, in the case where plants are in a growing period, the conditions which lead to the low temperature stress factor may be conditions in which an average cultivation temperature in an environment where plants are cultivated is 15° C. or lower, more severely 10° C. or lower, and still more severely 5° C. or lower. The present invention is capable of providing a method for reducing temperature stress of plants under these low temperature stress conditions. Reduction of the temperature stress of plants can be evaluated by measuring an improvement in the indicators which show the temperature stress.

In the present invention, it is possible to use, as indicators of the temperature stress, plant phenotypes such as (1) germination percentage, (2) seedling establishment rate, (3) number of healthy leaves, (4) plant length, (5) plant weight, (6) leaf area, (7) leaf color, (8) number or weight of seeds or fruits, (9) quality of harvests, (10) flower setting rate or fruit setting rate and (11) chlorophyll fluorescence yield.

The indicators can be measured in the following manner.

(1) Germination Percentage

Seeds of plants are sown, for example, in the soil, on a filter paper, on an agar culture medium or on sand, and allowed to undergo germination, and then the ratio of the number of germinations to the number of seeds is examined.

(2) Seedling Establishment Rate

Seeds of plants are sown, for example, in the soil, on a filter paper, on an agar culture medium or on sand, and then allowed to undergo cultivation for a given period of time. During the entire or partial cultivation period, temperature stress is applied, and the percentage of surviving seedlings is examined.

(3) Number of Healthy Leaves

With respect to plants, the number of healthy leaves is counted and the total number of healthy leaves is examined. Alternatively, the ratio of the number of healthy leaves to the number of all leaves of plants is examined.

(4) Plant Length

With respect to plants, the length from the base of the stem of the above-ground part to the branches and leaves at the tip is measured.

(5) Plant Weight

The above-ground part of each of plants is cut and the weight is measured to determine a fresh weight of plants. Alternatively, the cut sample is dried and the weight is measured to determine a dry weight of plants.

(6) Leaf Area

A photograph of plants is taken by a digital camera and the area of a green portion in the photograph is determined by image analysis software, for example, Win ROOF (manufactured by MITANI CORPORATION) to obtain a leaf area of plants.

(7) Leaf Color

After sampling leaves of plants, the chlorophyll content is measured using a chlorophyll gauge (for example, SPAD-502, manufactured by KONICA MINOLTA Holdings, Inc.) to determine the leaf color.

(8) Number or Weight of Seeds or Fruits

After cultivating plants until they bear fruits or fruits reach full maturity, the number of fruits per plant or the total fruit weight per plant is measured. After cultivating plants until seeds undergo ripening, elements constituting the yield such as the number of ears, ripening rate and thousand kernel weight are examined.

(9) Quality of Harvests

After cultivating plants until fruits reach full maturity, the quality of harvests is evaluated, for example, by measuring the sugar content of fully matured fruits using a saccharimeter.

(10) Flower Setting Rate, Fruit Setting Rate

After cultivating plants until they bear fruits, the number of flower setting and the number of fruit setting are counted to determine the fruit setting rate % (number of fruit setting/number of flower setting×100).

(11) Chlorophyll Fluorescence Yield

Using a pulse modulation chlorophyll fluorometer (for example, IMAGING-PAM manufactured by WALZ Company), the chlorophyll fluorescence (Fv/Fm) of plants is determined to obtain the chlorophyll fluorescence yield.

EXAMPLES

While the present invention will be more specifically described by way of formulation examples, seed treatment examples, and test examples in the following, the present invention is not limited to the following examples. In the following examples, the part represents part by weight unless otherwise specified.

Formulation Example 1

Fully mixed are 3.75 parts of the present compound, 14 parts of polyoxyethylene styrylphenyl ether, 6 parts of calcium dodecyl benzene sulfonate and 76.25 parts of xylene, so as to obtain an emulsion.

Formulation Example 2

Ten (10) parts of the present compound, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain a flowable formulation.

Formulation Example 3

Fifteen (15) parts of the present compound, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Formulation Example 4

Forty-five (45) parts of the present compound, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. One hundred and fifty (150) parts of glass beads (diameter=1 mm) are put into 100 parts of the slurry, and the slurry is ground for 2 hours while being cooled with a cooling water. After ground, the resultant is filtered to remove the glass beads and flowable formulation is obtained.

Formulation Example 5

Mixed to obtain an AI premix are 50.5 parts of the present compound, 38.5 parts of NN kaolin clay (manufactured by Takehara Chemical Industrial), 10 parts of MorwetD425 and 1.5 parts of MorwerEFW (manufactured by Akzo Nobel Corp.). This premix is ground with a jet mill so as to obtain a powder formulation.

Formulation Example 6

Five (5) parts of the present compound, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain a granule formulation.

Formulation Example 7

Three (3) parts of the present compound, 87 parts of kaolin clay and 10 parts of talc are fully ground and mixed so as to obtain a powder formulation.

Formulation Example 8

Twenty-two (22) parts of the present compound, 3 parts of calcium lignin sulfonate, 2 parts of sodium lauryl sulfate and 73 parts of synthetic hydrated silicon oxide are fully ground and mixed so as to obtain wettable powders.

Seed treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable formulation prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable formulation prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

Five (5) parts of a flowable formulation prepared as in Formulation example 4, 5 parts of pigment BPD6135 (manufactured by Sun Chemical) and 35 parts of water are mixed to prepare a mixture. The mixture is used for smear treatment in an amount of 60 ml per 10 kg of dried cotton seeds using a rotary seed treatment machine (seed dresser, produced by Hans-Ulrich Hege GmbH) so as to obtain treated seeds.

Seed Treatment Example 5

A powder agent prepared as in Formulation example 5 is used for powder coating treatment in an amount of 50 g per 10 kg of dried corn seeds so as to obtain treated seeds.

Seed Treatment Example 6

A powder agent prepared as in Formulation example 7 is used for powder coating treatment in an amount of 40 g per 100 kg of dried rice seeds so as to obtain treated seeds.

Seed Treatment Example 7

A flowable formulation prepared as in Formulation example 2 is used for smear treatment in an amount of 50 ml per 10 kg of dried soybean seeds using a rotary seed treatment machine (seed dresser, produced by Hans-Ulrich Hege GmbH) so as to obtain treated seeds.

Seed Treatment Example 8

A flowable formulation prepared as in Formulation example 3 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of sunflower seeds using a rotary seed treatment machine (seed dresser, produced by Hans-Ulrich Hege GmbH) so as to obtain treated seeds.

Seed Treatment Example 11

A powder agent prepared as in Formulation example 5 is used for powder coating treatment in an amount of 40 g per 10 kg of dried sugar beet seeds so as to obtain treated seeds.

Test Example 1

Evaluation Test for Reduction of High Temperature Stress in Hydroponics of Tomato (Number of Healthy Leaves)

<Test Plants>

Tomato seeds (cultivar: PATIO) were sown on a hydroponic sponge and then cultivated for 3 to 4 weeks under the conditions of a temperature of 22 to 25° C., a humidity of 55 to 75%, an illuminance of 5,000 lx and a day length of 16 hours, using 1,000-times diluted HYPONeX (HYPONeX JAPAN CORP., LTD.) as a hydroponic culture medium. A seedling of tomato at the 3rd leaf stage was tested.

<Application of the Present Compound>

With respect to the compound A, the compound B, the compound C, the compound D, the compound E, the compound F and the compound G, a DMSO solution having a concentration 10,000 times of each test concentration was prepared, and 10 µL of the obtained DMSO solution was added to 100 ml of distilled water to obtain a test liquid. An aqueous solution having a concentration of 250,000 ppm of a sodium salt of the compound A was prepared and the obtained aqueous solution was added to 100 ml of distilled water so as to give each test concentration, and then, 10 µL of DMSO was added thereto to obtain a test liquid. As a control, an aqueous solution as a test liquid was prepared by adding 10 µL of DMSO to 100 ml of distilled water.

Next, 100 ml of each test liquid and three of the above test plants were put in a square-shaped cup (C-AP square cup 88-200Mi, manufactured by Chuo Kagaku Co., Ltd.) and then cultivated for 2 days under the conditions of a temperature of 22 to 25° C., a humidity of 55 to 75%, an illuminance of 5,000 lx, and a light period of 16 hours/a dark period of 8 hours.

<High Temperature Stress Test>

The above test plants to which each test liquid was applied were put in an artificial climate chamber set to the following conditions, and a stress test was carried out. Temperature: 50° C., 5 hours, Illuminance: 6,500 to 7,900 lx, and Humidity: 50%.

<Evaluation>

After the above high temperature stress test, the number of healthy leaves (2 cotyledons and 3 true leaves) of each test plant was counted and each test plants was assigned a score from 0 to 5 with a score of 0 representing complete death and with a score of 5 representing having healthy leaves equally to the case before the stress treatment. After combining scores of three test plants, the test results of the group to which aqueous solutions of the respective compounds have been applied were compared with the test results of the group to which an aqueous solution containing only DMSO added therein (control) has been applied. As a result, the number of healthy leaves of plants in the cups to which aqueous solutions of the respective compounds were applied (test group of the present invention) was apparently larger than that in the case of control and temperature stress was reduced.

Test Example 2

Evaluation Test for Reduction of High Temperature Stress by Wheat Seed Treatment (Plant Weight)

<Seed Treatment>

A Blank slurry solution containing 5% (V/V) color coat red (Becker Underwood, Inc.), 5% (V/V) CF-Clear (Becker Underwood, Inc.) and 0.4% Maxim XL (Syngenta) was prepared. A sodium salt of the compound A was dissolved in the Blank slurry to obtain a slurry solution so as to control the amount of the sodium salt within a range from 0.5 mg to 2 mg per 1 g of seeds. Using a seed treating machine (HEGE11, manufactured by Hans-Ulrich Hege), seed coating was carried out by mixing 1.3 ml of the slurry solution with 50 g of wheat seeds (cultivar: Apogee) and the seeds were dried. As a control, seed coating was carried out using the Blank slurry solution in place of the slurry solution to obtain seeds for non-treated group. The coated seeds (5 seeds each) were sown in the growing soil (AISAI) in a plastic pot and then cultivated for 18 days under the conditions of a temperature of 20 to 25° C., a humidity of 50 to 75%, an illuminance of 5,300 lx, and a day length of 16 hours. Before the stress test, thinning was carried out to control the number of seedlings to 3 per pot.

<High Temperature Stress Test>

The above test plants on the 18th day after seeding were cultivated for 14 days under the conditions of a temperature of 40° C. (day)/30° C. (night), a humidity of 63% (day)/70% (night), an illuminance of 7,100 lx, and a day length of 16 hours.

<Evaluation Method>

After the stress test, on the 32nd day after seeding, fresh weight of the above-ground part of test plants was examined for 4 to 7 pots. The results are shown in Table 1.

TABLE 1

| Test compound | Amount of chemical (mg/g of seeds) | Fresh weight of the above-ground part (mg/3 seedlings) | Percentage relative to non-treated group (%) |
|---|---|---|---|
| None (=non-treated group) | 0 | 0.57 | 100 |
| Compound A, Na salt | 0.5 | 0.87 | 150 |
|  | 1.0 | 0.77 | 140 |
|  | 2.0 | 0.81 | 140 |

Test Example 3

Evaluation Test for Reduction of High Temperature Stress by Wheat Foliage Spraying Treatment (Plant Weight)

<Test Plants>

Wheat (cultivar: Apogee) seeds were sown in the growing soil (AISAI) in a plastic pot (955 mm×58 mm in height) and then cultivated for one week under the conditions of a temperature of 20 to 25° C., a humidity of 50 to 75%, an illuminance of 5,300 lx, and a day length of 16 hours.

<Application of the Present Compound>

A flowable formulation of the compound A was obtained by adding about 120 mg of a mixture of white carbon and a polyoxyethylene alkyl ether sulfate ammonium salt (weight ratio of 1:1) and 300 µl of water to 0.5 mg of the compound A, followed by fine grinding using a wet grinding method. The obtained flowable formulation was diluted with 50 ml of water to obtain a spray liquid. After adding 0.2% RINO as a sticker to the spray liquid, a sufficient amount (45 ml per 6 pots) was sprayed using an automatic spraying machine. As a control, a flowable formulation not containing the compound A was prepared and then sprayed to the non-treated group. Under the conditions of a temperature of 20 to 25° C., a humidity of 50 to 75%, an illuminance of 5,300 lx, and a day length of 16 hours, cultivation was carried out for 2 days.

<High Temperature Stress Test>

The above test plants having been subjected to the spraying treatment were put in an artificial climate chamber set to the following conditions, and a stress test was carried out.
Temperature: 45° C., 17 hours, Illuminance: 6,500 to 7,900 lx, and Humidity: 50%.

<Evaluation Method>

After the stress test, test plants were cultivated for 4 days under the conditions of a temperature of 20 to 25° C., a humidity of 50 to 75%, an illuminance of 5,300 lx, and a day length of 16 hours, visual evaluation was carried out and a fresh weight of the above-ground part was examined. As a result, in the group treated with the compound A, as compared with the non-treated group, alleviation of high temperature stress-induced withering and dying was observed in visual evaluation, and also the fresh weight of the above-ground part increased.

Test Example 4

Evaluation Test for Reduction of High Temperature Stress by Tomato Soil Irrigation Treatment (Fruit Setting Rate)

<Test Plants>

Tomato seeds (cultivar: Micro-Tom) were sown in the growing soil (AISAI) in a plastic pot and then cultivated in a greenhouse (set at a temperature of 25° C.) for about 4 weeks.

<Application of the Present Compound>

A soil irrigation treatment was carried out twice, using an aqueous solution of a sodium salt of the compound A in an amount of 50 ml per seedling, on the 15th day and the 22nd day after seeding. As a control, a soil irrigation treatment was carried out using distilled water in an amount of 50 ml per seedling to form a non-treated group.

<High Temperature Stress Test>

After the irrigation treatment, plants cultivated up to the period when a 1st flower cluster blooms (1 to 2 flowers bloom(s), on the 32nd day after seeding) were cultivated for 7 days under the conditions of a temperature of 40° C. (day)/30° C. (night), a humidity of 63% (day)/70% (night), an illuminance of 7,100 lx, and a day length of 16 hours in the stress exposed group, while plants were cultivated for 7 days in a greenhouse (set at a temperature of 25° C.) in the stress non-exposed group.

<Evaluation>

After the stress test, the test plants were cultivated for 13 days in a greenhouse (set at a temperature of 25° C.), the number of flower setting and the number of fruit setting were counted to determine a fruit setting rate (%) (number of fruit setting/number of flower setting×100). While the fruit setting rate decreased due to high temperature stress exposure in the non-treated group, a decrease in fruit setting rate was remarkably alleviated in the group treated with the compound A as compared with the non-treated group.

Test Example 5

Evaluation Test for Reduction of High Temperature Stress by Tomato Spraying Treatment (Number or Weight of Seeds or Fruits, Fruit Setting Rate)

<Test Plants>

Tomato seeds (cultivar: Micro-Tom) are sown in the growing soil (AISAI) in a plastic pot and then cultivated for about 4 weeks in a greenhouse (set at a temperature of 25° C.) up to the period when a 1st flower cluster blooms (one to two flowers bloom(s)).

<Application of the Present Compound>

After adding 0.2% RINO as a sticker to an aqueous solution of any one of the compounds A to G, the solution is sprayed to the entire test plants in an amount of 10 ml per seedling.

The above compound solution is sprayed to foliages of the test plants in an amount of 10 ml per seedling. After the spraying treatment, the test plants are air-dried for about 2 hours.

As a control, a spraying treatment is carried out in the same manner, using distilled water containing only 0.2% RINO as a sticker added therein to form a non-treated group.

<High Temperature Stress Test>

The test plants having been subjected to the spraying treatment are cultivated for 7 days under the conditions of a temperature of 40° C. (day)/30° C. (night), a humidity of 63% (day)/70% (night), an illuminance of 7,100 lx, and a day length of 16 hours.

<Evaluation>

After the stress test, the test plants are cultivated for about 2 weeks in a greenhouse (set at a temperature of 25° C.). The number of flower setting and the number of fruit setting are counted to determine a fruit setting rate (%) (number of fruit setting/number of flower setting×100). The diameters of fruits are measured and the average is determined. After the stress test, the plants are cultivated until fruits are fully matured and the total weight of the fruits is examined.

In the group treated with the present compound, as compared with the non-treated group, an increase in the fruiting rate, an increase in the number of fruits, an increase in the diameter of fruits, and an increase in the total weight of fruits are observed.

Test Example 6

Evaluation Test for Reduction of High Temperature Stress by Wheat Spike Spraying Treatment (Number or Weight of Seeds or Fruits)

<Test Plants>

Wheat seeds (cultivar: Perigee or Apogee) are sown in the growing soil (AISAI) in a plastic pot, and cultivated for about 4 weeks in a greenhouse (set at a temperature of 25° C.) up to an earing period.

<Application of the Present Compound>

After adding 0.2% RINO as a sticker to an aqueous solution of any one of the compounds A to G, the solution is sprayed to the entire plants several times every other week starting from 7 days before blooming in an amount of 10 ml per seedling. As a control, a spraying treatment is carried out in the same manner, using distilled water containing only 0.2% RINO as a sticker added therein to form a non-treated group.

<High Temperature Stress Test>

The test plants having subjected to the spraying treatment are cultivated for 14 days under the conditions of a temperature of 32° C. (day)/22° C. (night), a humidity of 63% (day)/70% (night), an illuminance of 7,100 lx, and a day length of 16 hours.

<Evaluation Method>

After the stress test, the test plants are cultivated in a greenhouse (set at a temperature of 25° C.) until grain filling and the grain weight is examined. In the group treated with the present compound, as compared with the non-treated group, an increase in the grain weight is observed.

Test Example 7

Evaluation Test for Reduction of High Temperature or Low Temperature Stress in Hydroponics of *Arabidopsis* (Seedling Establishment Rate, Leaf Area, Chlorophyll Fluorescence Yield)

<Test Plants>

A hydroponic sponge piece (1 cm×1 cm×0.2 cm) is immersed with an MS culture medium (containing 2.5 mM MES, 2% sucrose, and a 1,000 times diluted Gamborg vitamin solution G1019 (manufactured by Sigma-Aldrich Corporation)) and 5 to 8 *Arabidopsis* (ecotype Columbia) seeds having been subjected to surface sterilization are sown on the sponge. After the low temperature treatment (at 4° C. for 2 to 4 days), cultivation is carried out for 6 days under the conditions of a temperature of 23° C., a humidity of 45%, an illuminance of 3,500 lx, and a light period of 16 hours/a dark period of 8 hours.

<Transplantation and Application of the Present Compound>

In a 24-well plate (SUMILON MS-80240), 0.5 ml each of an MS culture medium, which is a culture medium containing 2.5 mM MES, 2% sucrose and a 1,000 times diluted Gamborg vitamin solution G1019 (manufactured by Sigma-Aldrich Corporation), containing any one of the compounds A to G having a concentration of 0.01 to 100 ppm is dispensed, and then a sterilized cotton wool is spread on each well. After thinning the above *Arabidopsis* seedlings to 1 to 2 per sponge, the seedlings are transplanted to each well together with the sponge and then grown overnight.

The above "MS culture medium containing the test compound" is prepared in the following manner. That is, with respect to the compound A, the compound B, the compound C, the compound D, the compound E, the compound F or the compound G, a DMSO solution having a concentration 1,000 times of each test concentration is prepared, and 0.5 μL of the obtained DMSO solution is added to 0.5 ml of the MS culture medium. An aqueous solution (250,000 ppm) of a sodium salt of the compound A is prepared and the obtained aqueous solution is added to 0.5 ml of the MS culture medium so as to give each test concentration, and then 0.5 μL of DMSO is added to 0.5 ml of the culture medium. As a control, an MS culture medium containing 0.1% DMSO added therein is prepared to form a non-treated group.

<High Temperature Stress Test>

A lidded 24-well plate is sealed with a film, followed by immersion in a water incubator and further incubation at 45° C. for 60 minutes.

<Low Temperature Stress Test>

A lidded 24-well plate is sealed with surgical tape, followed by cultivation for 6 days under the conditions of a temperature of 0 to 1° C., a humidity of 40 to 70%, an illuminance of 3,000 lx, and a light period of 16 hours/a dark period of 8 hours.

<Evaluation>

After the stress test, the test plants are cultivated for 3 to 5 days under the conditions of a temperature of 23° C., a humidity of 45%, an illuminance of 3,500 lx, and a light period of 16 hours/a dark period of 8 hours. A photograph of each well is taken by a digital camera and the area of the green portion of the photograph is determined by imageing analysis software Win ROOF (manufactured by MITANI CORPORATION) to determine the size of the plant body. One day after the high temperature stress test, the chlorophyll fluorescence (Fv/Fm) of each well is measured using a pulse modulation chlorophyll fluorometer (IMAGING-PAM, manufactured by WALZ Company).

In each group treated with the present compound, as compared with the non-treated group, plants become large and growth acceleration of the above-ground part is observed. In each group treated with the present compound, as compared with the non-treated group, an increase in the chlorophyll fluorescence is observed.

Test Example 8

Evaluation Test for Reduction of Low Temperature Stress by Corn Perfusion Treatment (Plant Weight, Chlorophyll Fluorescence Yield, Leaf Color)

<Test Plants>

Corn seeds (cultivar: PIONEER 120 31P41) are sown in the growing soil (AISAI) in a plastic pot and then cultivated for 7 days under the conditions of a temperature of 20 to 25° C., a humidity of 50 to 75%, an illuminance of 4,500 lx, and a day length of 16 hours.

<Application of the Present Compound>

A DMSO solution having a concentration 1,000 times of each test concentration of any one of the compounds A to G is prepared and then diluted with distilled water. An aqueous solution (250,000 ppm) of a sodium salt of the compound A is diluted to prepare a test liquid. After soil perfusion is carried out around the seedling of the above test plants using 50 ml of the test liquid thus prepared, the test plants are cultivated for 2 days under the conditions of a temperature of 20 to 25° C., a humidity of 50 to 75%, an illuminance of 4,500 lx, and a day length of 16 hours.

Using distilled water containing 0.1% DMSO added therein as a control of any one of the compounds A to G and using distilled water as a control of the sodium salt of the compound A, the soil perfusion treatment is carried out in the same manner to form a non-treated group.

<Low Temperature Stress Test>

The above test plants subjected to the soil perfusion are cultivated for 5 days under the conditions of a temperature of 2 to 4° C., a humidity of 40 to 70%, an illuminance of 3,500 lx, and a light period of 16 hours/a dark period of 8 hours.

<Evaluation>

After the stress test, the test plants are cultivated for 4 days under the conditions of a temperature of 20 to 25° C., a humidity of 50 to 75%, an illuminance of 4,500 lx, and a day length of 16 hours, and the plant weight and the length of true leaves are measured. One day after the stress test, the chlorophyll fluorescence (Fv/Fm) is measured using a pulse modulation chlorophyll fluorometer (MAXI-IMAGING-PAM, WALZ). Using a chlorophyll gauge (SPAD-502, manufactured by KONICA MINOLTA Holdings, Inc.), the chlorophyll content is measured.

In each group treated with the present compound, as compared with the non-treated group, the length of true leaves and the plant weight increase and growth acceleration of the above-ground part is observed. In each group treated with the present compound, as compared with the non-treated group, an increase in the chlorophyll fluorescence and an increase in the chlorophyll content are observed as compared with the non-treated group.

Test Example 9

Evaluation Test for Reduction of Low Temperature Stress in Hydroponics of Rice (Plant Length, Plant Weight, Chlorophyll Fluorescence Yield)

<Test Plants>

Rice seeds (cultivar: NIHOMBARE) are immersed in distilled water containing 1,000 ppm of Benlate and then incubated at 30° C. for one day. The seeds are washed with distilled water, incubated in distilled water for one day and then subjected to a forced germination treatment. In the bottom of a 288-well plug tray, cotton wool is spread and then the seeds subjected to the forced germination treatment are sown. A hydroponic culture medium (8-fold diluted Kimura B hydroponic culture solution) is added thereto, followed by cultivation for 3 to 10 days under the conditions of a temperature of 28° C. (day)/23° C. (night), a humidity of 60%, an illuminance of 7,100 lx, and a day length of 12 hours.

<Application of the Present Compound>

A DMSO solution having a concentration 1,000 times of each test concentration of any one of the compounds A to G is prepared and then diluted with a hydroponic culture medium. An aqueous solution (250,000 ppm) of a sodium salt of the compound A is diluted with the hydroponic culture medium to prepare a liquid having a test concentration. The above rice seedling is transferred to these hydroponic culture media containing the compound, and then cultivated for 7 to 10 days under the conditions of a temperature of 28° C. (day)/23° C. (night), a humidity of 60%, an illuminance of 7,100 lx, and a day length of 12 hours.

Using a hydroponic culture medium containing 0.1% DMSO added therein as a control of any one of the compounds A to G and using a hydroponic culture medium as a control of the sodium salt of the compound A, the above rice seedlings are cultivated to form a non-treated group.

<Low Temperature Stress Test>

The seedlings during the treatment with the present compound are cultivated for 3 to 7 days under the conditions of a temperature of 2 to 4° C., a humidity of 40 to 70%, an illuminance of 3,500 lx, and a day length of 12 hours in the stress exposed group, and under the conditions of a temperature of 25 to 30° C., a humidity of 50 to 75%, an illuminance of 4,500 lx, and a day length of 12 hours in the stress non-exposed group.

<Evaluation>

After the stress test, the plant length and the weight of the above-ground part are examined. Using a pulse modulation chlorophyll fluorometer (MAXI-IMAGING-PAM, WALZ), the chlorophyll fluorescence (Fv/Fm) is measured.

In the stress exposed group, as compared with the stress non-exposed group, control of the plant length, a decrease in weight of the above-ground part and a decrease in the chlorophyll fluorescence in the non-treated group are observed. In the stress exposed group, in the group treated with a Na salt of the compound A or the compound B, as compared with the non-treated group, the plant length, the weight of the above-ground part and the chlorophyll fluorescence increase.

Test Example 10

Evaluation Test for Reduction of High Temperature Stress by Wheat Seed Treatment (Plant Weight)

<Seed Treatment>

A Blank slurry solution containing 5% (V/V) color coat red (Becker Underwood, Inc.), 5% (V/V) CF-Clear (Becker Underwood, Inc.) and 0.4% Maxim XL (Syngenta) was prepared. The compound C (methyl 4-oxo-4-(2-phenylethyl)aminobutyrate) or the compound E (5-oxo-5-[2-(3-indolyl)ethyl]aminovaleric acid) was dissolved in the Blank slurry to obtain a slurry solution so as to control the amount of the compound to be 5 mg per 1 g of seeds. Using a 50-ml conical tube, seed coating was carried out by mixing 1.3 ml of the slurry solution with 50 g of wheat seeds (cultivar: Apogee) and the seeds were dried. As a control, seed coating was carried out using the Blank slurry solution in place of the slurry solution to obtain seeds for non-treated group. The coated seeds (5 seeds each) were sown in the growing soil (AISAI) in a plastic pot and then cultivated in a greenhouse (set at a temperature of 18° C. (day)/15° C. (night)) for 17 days. Before the stress test, thinning was carried out to control the number of seedlings to 3 per pot.

<High Temperature Stress Test>

The above test plants on the 17th day after seeding were cultivated for 19 days in an artificial climate chamber under the conditions of a temperature of 36° C. (day)/32° C. (night), a humidity of 50% (day)/60% (night), an illuminance of 7,000 lx, and a day length of 12 hours.

<Evaluation Method>

After the stress test, on the 36nd day after seeding, fresh weight of the above-ground part of test plants was examined for 7 to 9 pots. In the group treated with the compound C or the compound E, as compared with the non-treated group, the fresh weight of the above-ground part increased.

INDUSTRIAL APPLICABILITY

Use of the method of the present invention enables relief of temperature stress of plants.

The invention claimed is:

1. A method for reducing temperature stress of plants which comprises applying an effective amount of one or more compounds selected from the group consisting of the compounds defined below in a seed treatment, which is from 50 g to 200 g per 100 kg of seeds and an agriculturally acceptable salt thereof to a plant that has been exposed to or to be exposed to a temperature stress factor:
   (1) 4-oxo-4-(2-phenylethyl)aminobutyric acid,
   (2) methyl 4-oxo-4-(2-phenylethyl)aminobutyrate, and
   (3) 4-oxo-4-(4-phenylbutyl)aminobutyric acid;
   wherein the plant is corn or wheat.

2. The method according to claim 1, wherein the plant is a transgenic plant.

3. The method according to claim 1, wherein the temperature stress is high temperature stress.

4. The method according to claim 1, wherein the temperature stress is low temperature stress.

5. The method according to claim 1, wherein the temperature stress is indicated by a change in one or more of the following plant phenotypes:
   (1) germination percentage,
   (2) seedling establishment rate,
   (3) number of healthy leaves,
   (4) plant length,
   (5) plant weight,
   (6) leaf area,
   (7) leaf color,
   (8) number or weight of seeds or fruits,
   (9) quality of harvests,
   (10) flower setting rate or fruit setting rate, and
   (11) chlorophyll fluorescence yield.

\* \* \* \* \*